United States Patent [19]
Poissant et al.

[11] Patent Number: 5,658,801
[45] Date of Patent: Aug. 19, 1997

[54] MEDICAL TEST KIT

[75] Inventors: Philip Poissant; Peter Lea, both of Toronto, Canada

[73] Assignee: Spectral Diagnostics Inc., Toronto, Canada

[21] Appl. No.: 368,791

[22] Filed: Jan. 4, 1995

Related U.S. Application Data

[63] Continuation-in-part of Ser. No. 237,374, May 3, 1994, abandoned.

[51] Int. Cl.$^6$ .................... G01N 33/543; G01N 33/558
[52] U.S. Cl. .................. 436/518; 422/55; 422/56; 422/57; 422/58; 422/61; 422/101; 422/102; 435/287.1; 435/287.2; 435/287.7; 435/287.9; 435/288.4; 435/288.5; 435/810; 435/970; 435/975; 436/574; 436/805; 436/810
[58] Field of Search ................... 422/55–58, 61, 422/99, 101, 102; 435/810, 970, 975, 287.1, 287.2, 287.7, 287.9, 288.4, 288.5; 436/518, 514, 805, 810

[56] References Cited

U.S. PATENT DOCUMENTS

| | | |
|---|---|---|
| 4,912,034 | 3/1990 | Kalra et al. . |
| 4,943,522 | 7/1990 | Eisinger et al. . |
| 4,981,786 | 1/1991 | Dafforn et al. . |
| 5,036,569 | 8/1991 | Linnecke . |
| 5,096,575 | 3/1992 | Cosack . |
| 5,149,622 | 9/1992 | Brown et al. . |
| 5,290,678 | 3/1994 | Jackowski . |
| 5,334,538 | 8/1994 | Parker et al. ............... 436/525 |

FOREIGN PATENT DOCUMENTS

| | | |
|---|---|---|
| 0260965 | 3/1988 | European Pat. Off. . |
| 0264036 | 4/1988 | European Pat. Off. . |
| WO92/12425 | 7/1992 | WIPO . |

Primary Examiner—Christopher L. Chin
Attorney, Agent, or Firm—Klauber & Jackson

[57] ABSTRACT

A medical diagnostic test kit includes a rectangular flat bottom member having an external raised flange and an internal raised flange forming a cavity therein; an elongated dry chemistry membrane held within the cavity; an arcuate cover member secured to the bottom member with the membrane therebetween; and a funnel assembly comprising a funnel member removably attached to the cover member with its nozzle portion extending into a sample opening in the cover member.

17 Claims, 6 Drawing Sheets

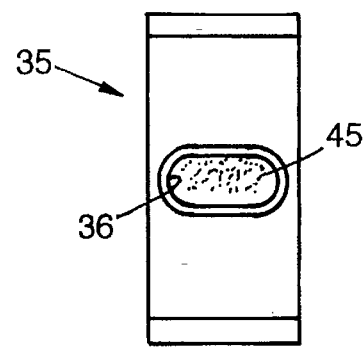
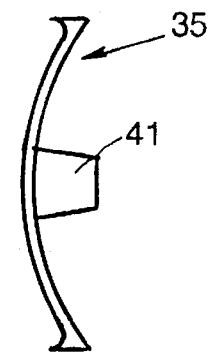
FIG. 9  FIG. 10
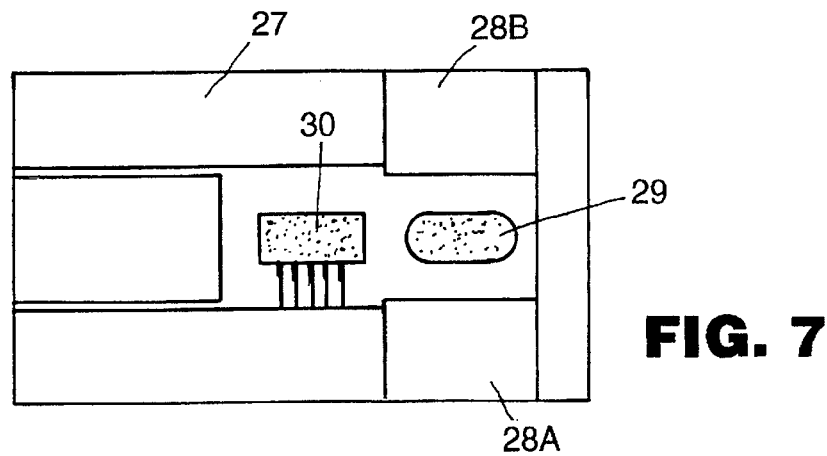
FIG. 8  FIG. 7
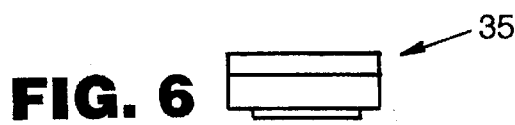
FIG. 6
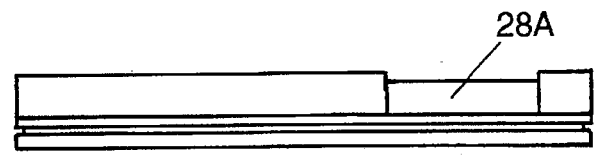
FIG. 5

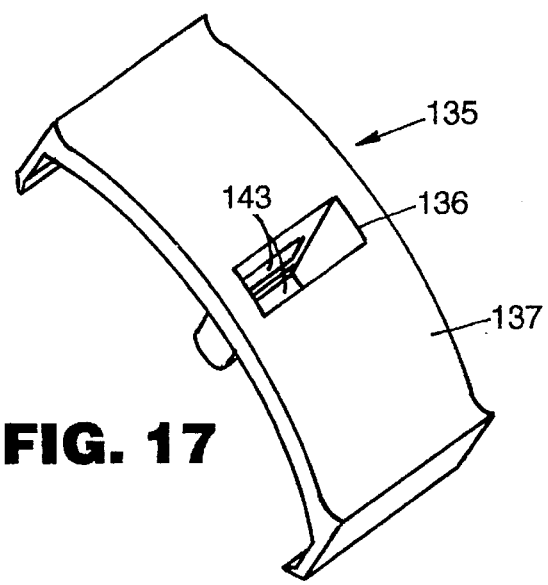
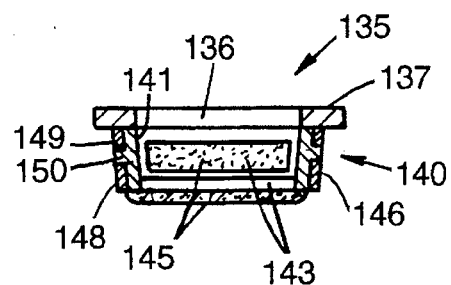
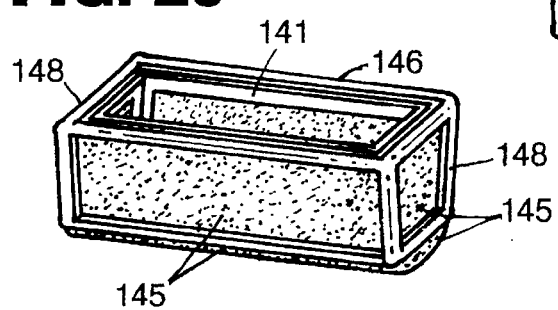
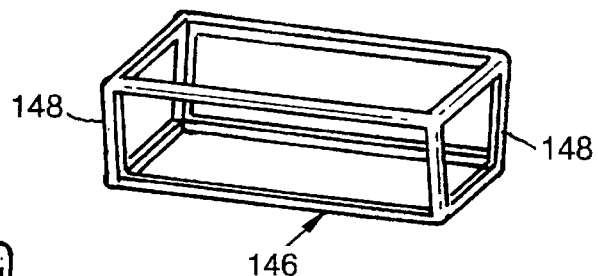
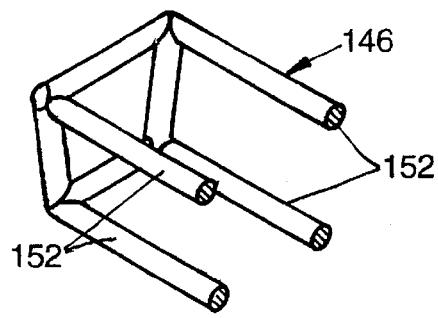
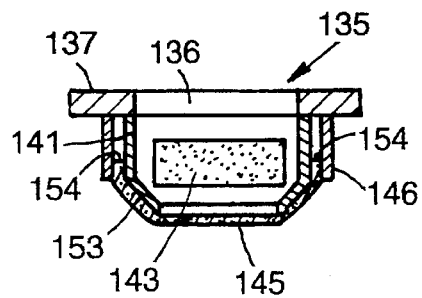
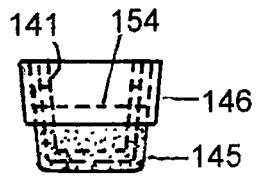

MEDICAL TEST KIT

CROSS REFERENCE TO RELATED APPLICATION

The present application is a Continuation-In-Part of application Ser. No. 08/237,374 filed May 3, 1994 by the inventor herein, now abandoned. Applicant claims the benefit thereof under 35 U.S.C. 120.

FIELD OF THE INVENTION

The present invention related to medical test kits and more particularly to the structure of diagnostic test kits.

BACKGROUND OF THE INVENTION

Medical diagnostic test kits come in numerous forms, depending primarily upon the reagents that are used in the test. For example, frequently the reagents are liquid and the test kit includes one or more bottles of the testing reagent.

Other types of diagnostic tent kits rely on reagents that are held within a solid matrix. For example, U.S. Pat. No. 5,290,678, entitled "Diagnostic Kit For Diagnosing and Distinguishing Chest Pain In Early Onset Thereof" (incorporated herein by reference) describes a diagnostic test kit employing a dry chemistry membrane. That membrane is positioned between front and back plastic panels. Although that patent describes an excellent diagnostic panel, to determine cardiac damage by determining the presence of cardiac analytes in a patient's blood, improvements may be made in terms of convenience of use of the teat kit and its use for various types of tests.

More particularly, the test kit includes a separating membrane that serves as the initial recipient and filter for the liquid specimen. The role of this membrane is to convey the essential components of the specimen to the test strip for the performance of the assay while filtering out, if possible, unwanted components such as particulates, that may be present in the initial specimen as drawn. One of the difficulties with the fabrication of the device is the fragility of the separating membrane, and its consequent tendency to rupture or offer a discontinuous surface. During manufacture, particularly of devices where the membrane is disposed in curved relationship about the funnel, wrinkles frequently form, or the membrane raptures during securement against the funnel. The result in either event is reduced productivity and failure in use, and correspondingly increased per unit cost and reduced desirability of the product.

Other devices are known as represented by U.S. Pat. No. 4,943,522 to Eisinger et al. and U.S. Pat. No. 5, 149,622 to Brown et at. that purport to provide devices to serve as self-contained devices for the performance of an immunoassay for the analysis, for example, of a blood or like liquid sample. The devices disclosed in both references, however, are of complex construction and correspondingly limited capabilities. For example, the Eisinger et al. device uses a test membrane which is of compound curvature and is thus more bulky. Also, the Eisinger et al. device is incapable of disassembly after the specimen has been deposited, and this mandates that the portion of the specimen that would be preferably discarded after the sample is deposited, must be retained. The Brown et al. device suffers from a like drawback, in that the inlet for the deposit of the specimen is fixed to the remainder of the device, and the test strip is thus maintained in registry with the non-essential remainder of the specimen.

Neither of the constructions of Eisinger et al. or Brown et al. or any other construction known to the applicant herein, would work well with the test kit of Jackowski, particularly as the latter kit contemplates the easy removal of the test strip from the kit from the remainder of the device and the portion of the initial specimen that is to be discarded. A need therefore exists for a test kit device that that is capable of optimizing the speed and reliability of the Jackowski test kit, at a reduced cost and time expenditure.

SUMMARY OF THE INVENTION

The test kit of the present invention comprises a flat bottom member having a raised flange on its outside rectangular edges and having an inner raised flange forming a rectangular cavity. A test membrane, having suitable dry chemistry for the test to be performed, is in the form or an elongated strip. That strip is positioned within the rectangular cavity of the bottom member.

An arcuate cover member is positioned over the strip and the bottom member. The cover member has a rectangular flange which mates with the upstanding flange of the bottom member. The cover member has two elongated openings. The first opening is adapted for receipt of the patient's sample or body fluid and is positioned over one end of the test strip. The second elongated opening is a viewing port and permits the physician, or other medical personnel, to view the reaction of the patient's serum with the chemicals of the test strip.

In accordance with the present invention, the funnel assembly comprises the funnel holder which removably snaps into the first opening in the cover member, a funnel member disposed in communication with said funnel holder, which funnel member defines a nozzle portion for receiving a patient's body fluid or liquid specimen such as blood or serum, at least one opening for the egress of said body fluid, and a separation membrane located in wrinkle-free disposition against said funnel member and said nozzle portion for receiving said body fluid and delivering the same to the test membrane or strip. In a particular embodiment, the separation membrane is nonadhesively held in contact with said funnel member and said nozzle portion.

More particularly, the funnel assembly may include an outer frame or retainer member that is adapted to engage said funnel member and said nozzle portion, and to cooperate with said funnel member and said nozzle portion to wrap and hold said separation membrane in sandwich-like relationship therebetween. The outer frame or retainer may engage the funnel member snap-fittably or by a friction fit, within the scope of the invention.

In a variant embodiment, the kit comprises a plastic funnel assembly having three members. The first member is a funnel holder which removably snaps into the first opening in the cover member. A separate plastic elongated funnel member including a nozzle portion fits within the elongated opening of the snap-in member. The separationg membrane is retained at the bottom of the nozzle portion adjacent an egress opening defined therein.

In operation, a few drops of the patient's blood is taken from the patient and placed in the funnel member. The funnel member leads the blood, by gravity, to the separation membrane which retains the red blood cells and permits the flow-through of the patient's plasma without red blood cells to expedite the completion and subsequent interpretation of the test. The plasma flows by capillary action along the length of the elongated test membrane or strip and reacts, in sequence, with appropriate antibodies on the test membrane or strip. The snap-in portion may be removed while the test reactions are taking place as it is no longer useful. The physician, or other medical personnel, will then look through the second elongated opening of the cover member to determine whether the patient's plasma has caused a reaction. A suitable reaction indication is one, or a series, of colored stripes perpendicular to the length of the elongated test stripe, which become colored only if the antibodies of the stripe react with analytes in the patient's plasma.

Accordingly, it is a principal object of the present invention to provide a device to serve as part of a diagnostic test kit that is of simple and economical construction and reliability in use.

It is a further object of the present invention to provide a diagnostic test kit as aforesaid that rapidly and reliably receives a liquid medium suspected of containing one or more analytes under detection, and delivers the liquid medium rapidly and hygienically to an indicator substrate for deposition thereon.

It is a still further object of the present invention to provide a diagnostic test kit as aforesaid that is easily disassembled to retrieve the indicator substrate for evaluation by a medical technologist.

It is yet a further object of the present invention to provide a diagnostic test kit device that is of improved quality and durability during both manufacture and use.

Other objects and advantages will become apparent to those skilled in the art from a consideration of the ensuing detailed description taken in conjuction with the following illustrative drawings.

BRIEF DESCRIPTION OF THE DRAWINGS

FIG. 5 is a side plan view of the test kit prior to assembly;

FIG. 6 is an side plan view of the snap-in member;

FIG. 7 is a top plan view of the test kit prior to assembly;

FIG. 8 is an end plan view of the test kit of FIG. 7;

FIG. 9 is a top plan view of the snap-in member;

FIG. 10 is a side plan view of the snap-in member;

FIG. 17 is a perspective view of the funnel assembly of FIG. 15 taken from the top side thereof;

FIG. 18 is a side sectional view of the funnel assembly of FIG. 15;

FIG. 19 is a perspective view of a frame member in accordance with an alternate embodiment of the invention;

FIG. 20 is a perspective view taken from the top with the funnel holder not shown, of an assembled funnel assembly in accordance with the embodiment of FIG. 19;

FIG. 21 is a fragmentary perspective view of a frame member in accordance with an alternate embodiment of the invention;

FIG. 22 is a side sectional view similar to FIG. 18, showing a funnel assembly in accordance with an alternate embodiment of the invention; and FIG. 23 is a fragmentary end view partly in phantom, of the funnel assembly of FIG. 22.

DETAILED DESCRIPTION OF THE INVENTION

Figure 1:
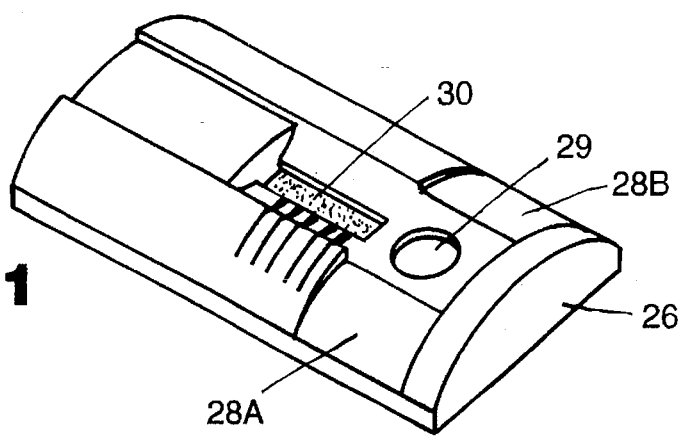
FIG. 1 is a perspective view of the test medical kit of the present invention, prior to assembly.
Figure 2:
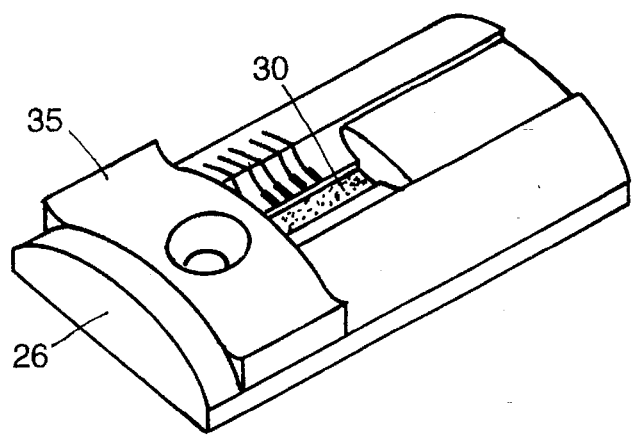
FIG. 2 is a perspective view of the test kit of FIG. 1, after assembly.
Figure 3:
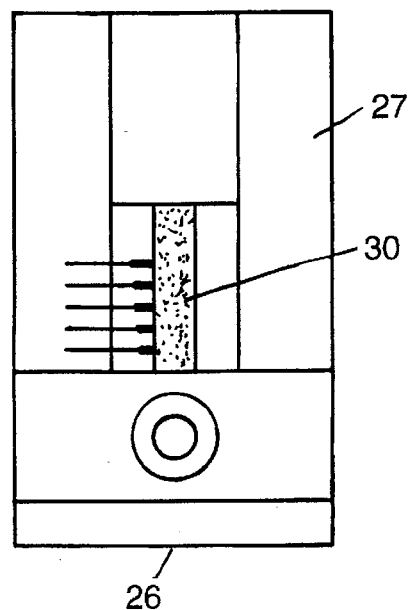
FIG. 3 is a top plan view of the test kit of FIG. 1, after assembly.
Figure 4:
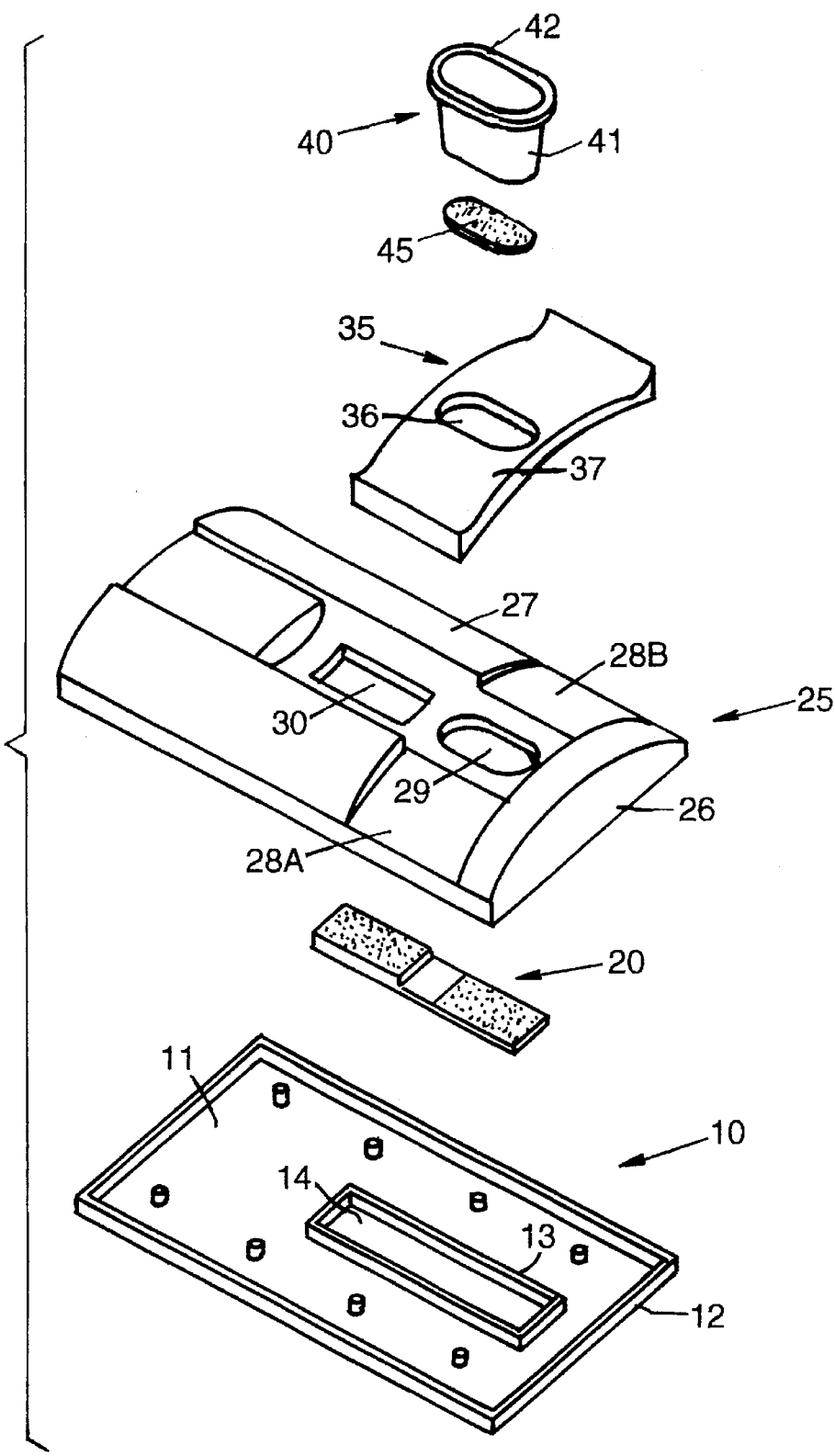
FIG. 4 is an exploded view of the test kit of FIG. 1 showing the arrangement of its parts.
Figure 11:
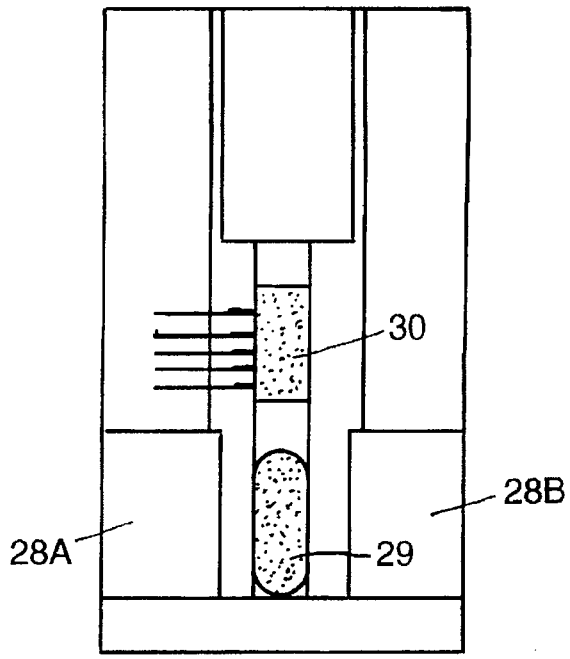
FIG. 11 is a top plan view of a multi-unit.
Figure 13:
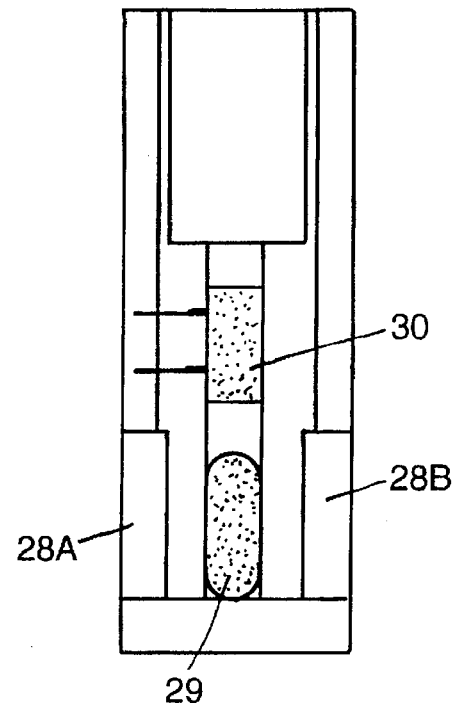
FIG. 13 is a top plan view of a single unit.
Figure 12:
FIG. 12 is an end plan view of the multi-unit of FIG. 11.
Figure 14:
FIG. 14 is an end plan view of the single unit of FIG. 13.

In accordance with the present invention there is provided a test kit for diagnostic medical purposes. The test kit is especially useful in connection with a test strip based upon the antigen/antibody reactions of the type disclosed in U.S. Pat. No. 5,290,678 referred to above.

The test kit comprises:

(i) a bottom member forming a flat bottom wall and having joinder means to join the bottom member to another member;

(ii) an elongated dry chemistry test membrane having at least one reagent which reacts with a patient's body fluid;

(iii) a cover member having joinder means to join the cover member to the bottom member and having a receiving opening to receive the body fluid and a display window opening to display at least part of the membrane; wherein the membrane is held between the bottom member and the cover member; and (iv) a removable funnel assembly comprising a funnel member having a nozzle portion adapted to extend and fit within the display window opening and into proximity with said test membrane, and means to removably attach the funnel assembly to the cover member.

The test kit includes a bottom member 10 which is rectangular in plan view. The bottom member 10, and the other structural members may be produced from a number of commercially available materials, including synthetic resins such as "ABS" (acrylonitrile-butadiene-styrene copolymers), polyolefins such as polypropylene, or polycarbonates, the foregoing being representative and not limitative hereof.

The bottom member 10 has a flat base 11 and an upstanding flange 12 which runs along the edge of the base 11 on its four sides. An elongated internal flange 13 forms an elongated rectangular cavity 14. A suitable representative and non-limitative size for the base may be 0.5 inches high, 2.0 inches wide and 3.5 inches long.

An elongated test strip 20 is positioned within the cavity 14. The test strip is a membrane which incorporates dry chemical reagents and may be supported on an absorbent strip of material. The reagents are adapted to react with components in the patient's plasma or other fluid which flows, by capillary action, along the length of the test strip 20.

A cover member 25 is adapted to fit over the test strip 20 and is secured on the bottom member. The cover member 25 has an arcuate end 26, an arcuate body portion 27, which may be rectangular, and two depressions 28A and 28B formed between the end 26 and the body portion 27.

The cover member 25 has a first elongated opening 29 (sample window) adapted to receive the patient's blood and has rounded ends. For example, each test may use 2–5 drops of blood. A second elongated opening 30 (display window), which may be rectangular, within the cover member 25, permits the physician or other medical personnel, to view the reaction between the patient's plasma and the dry chemical reagents of the test strip 20.

The funnel assembly of the invention may comprise a funnel holder including releasable attachment or fastening means for gripping said cover member to secure said funnel assembly thereagainst in use. A funnel member is disposed in said funnel holder and extends therefrom so as to facilitate communication with the receiving opening in said cover member. The funnel member defines a nozzle portion that is adapted to extend into said receiving opening as described. The funnel member and the nozzle portion thereof as illustrated herein appear to extend away from said funnel holder in a plane that is generally transverse to the major plane containing the funnel holder.

As used herein, the terms "funnel member" and "nozzle portion" associated therewith, are intended to cover structures that are of tapering design as contemplated by the colloquial meaning of "funnel", or of cylindrical or like tubular shape as contemplated by the colloquial meaning of "nozzle", as well as structures, some specifically illustrated herein, that are merely three-dimensional projections that, for example may be in the shape of a rhombus, a parallelogram or like structure where the walls are parallel to each other, skewed either toward or away from each other, or other such variations in shape. All such structures, including structures that arc largely skeletal in construction are included and contemplated within the spirit and scope of the present invention, and both terms as used herein should be accorded such correspondingly broad interpretation.

The funnel member and the nozzle portion thereof define at least one opening, and in a particular embodiment, plural openings for the passage therethrough of the liquid specimen enroute to its delivery to the dry chemistry test membrane. A separation membrane is disposed in fluid registry with said opening(s) to receive the liquid specimen and to convey the specimen to the test membrane, while in a particular embodiment, effecting a filtration of the specimen to remove unwanted and extraneous materials such as particulates therefrom. In accordance with the present invention, the separation membrane is adapted to extended arcuately about the funnel member and the nozzle portion, and likewise into maximal surface contact with the test membrane. Both features optimize uniformity, speed and extent of specimen delivery.

Figure 15:
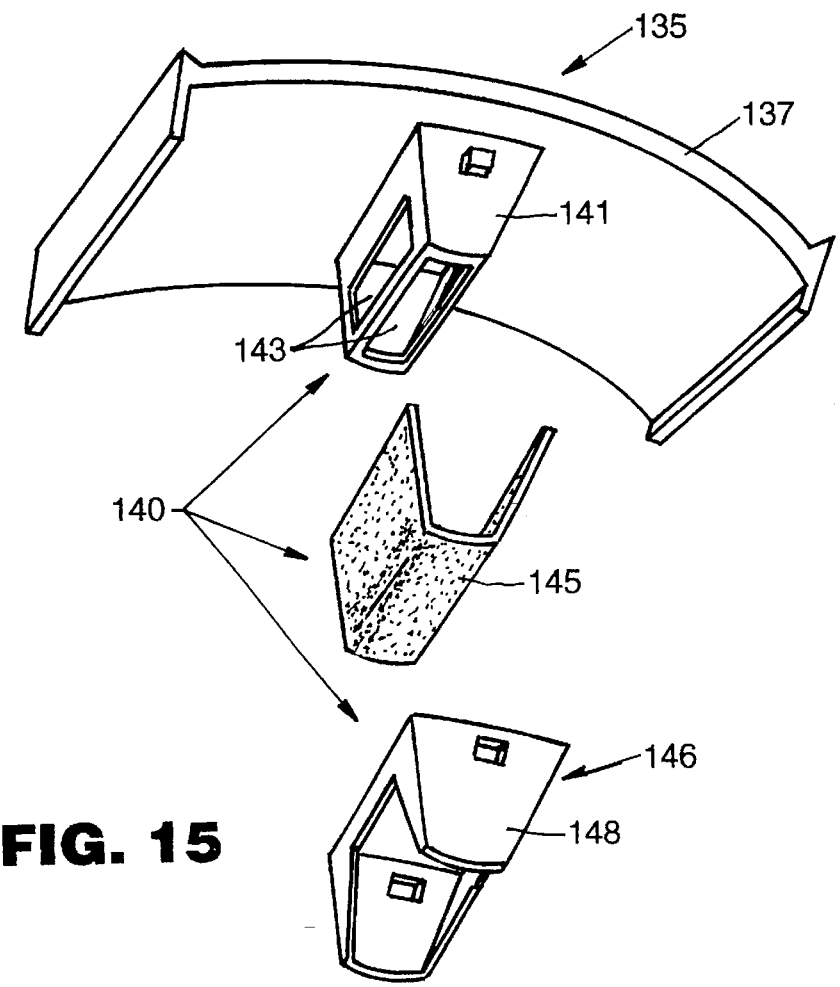
FIG. 15 is an exploded view in perspective of the underside of a funnel assembly in accordance with an alternate embodiment of the invention.

Referring to the drawings wherein like numerals denote like parts and particularly to FIGS. 15 through 23, a particular funnel assembly construction 135 is shown that comprises funnel holder 137 defining therein an opening 136 that as illustrated, is elongated and may appear rectangular in perimeter. The exact shape of opening is subject to variation in accordance with the invention, and all depictions are to be considered as illustrative and not limitative. Opening 136 is defined by funnel member 140 that may be at least partially integral with funnel holder 135. Funnel member 140 in turn, defines nozzle portion thereof 141 that defines at least one egress port 143 through which the specimen may exit. Referring to FIG. 15, nozzle portion defines three such egress ports 143, two of which are located on opposite walls of nozzle portion 141 and the third on the bottom. In this particular construction of funnel member 140 and nozzle portion 141, nozzle portion 141 appears almost skeletal, as it defines a framework that defines its three-dimensional shape and leaving large egress ports 143. A further variant of this construction can be seen in FIG. 19, A separation membrane 145 is disposed against funnel member 140 and nozzle portion 141 and into registry with egress port(s) 143. A feature of the invention is the ostensibly wrinkle-free compound curvature of separation membrane 145 as it wraps about nozzle potion 141. In a particular non-limitative embodiment, this is achieved in part by the particular construction of funnel member 140 that facilitates smooth disposition of the separation membrane 145 thereagainst. Thus, separation membrane 145 may be gently urged against the nozzle member 141 during assembly, for example, by the disposition thereover of an outer frame or retainer 146 that is a part of funnel member 140, and that cooperates with nozzle portion 141 to hold separation membrane in a sandwich-like engagement therebetween. Frame or retainer 146 may engage nozzle potion 141 by friction fit or by snap-fittable engagement, both as illustrated herein.

Figure 16:
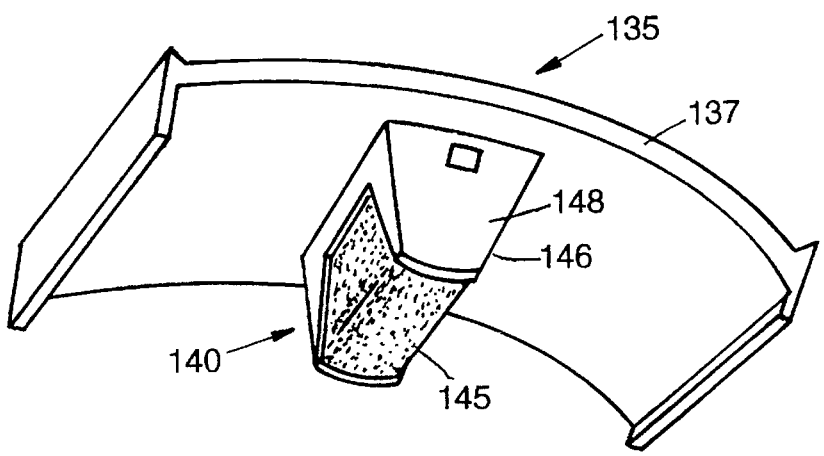
FIG. 16 is a perspective view similar to that Of FIG. 15 showing the funnel assembly as fully assembled.

Thus as shown in FIGS. 15, 16 and 18, frame 146 may define solid side panels 148 that may define either openings 149 to mate with corresponding projections 150 defined by the adjacent side walls of nozzle 141, or vice versa, the respective structures adapted in either event, to achieve a snap-fittable engagement with each other. Similarly, and as illustrated in FIGS. 19 and 20, the side panels 148 of both nozzle 141 and frame or retainer 146 may define openings in registry with each other, thereby relying on an extent of separation membrane 145 to define the wall thereof. In such event, the frame or retainer 146 and nozzle 141 are sized to achieve a friction fit against each other when the separation membrane is disposed therebetween.

A further feature of the present invention is the ability of the separation membrane 145 to achieve an optimal transfer of specimen to the test membrane. This is in part facilitated by the enhancement of surface juxtaposition between the respective membranes and the consequent increase in capillary flow between the two. Referring now to FIGS. 18 and 20, the compound curvature and projection of separation membrane 145 facilitates its maximal extent through receiving opening and into capillary registry with the adjacent surface of the test membrane when the device is fully assembled.

As mentioned earlier, frame or retainer may vary widely in its construction and shape within the scope of the invention. Thus, and with reference to FIG. 21, a representative frame 146 is shown that defines along its perimeter proximate to funnel holder 137 in full assembly, a capturing rim 152 that defines along at least a part of the circumference thereof a rounded cross-section. Though not wishing to be bound to a particular theory of operation or construction, it is considered that the curvature of capturing rim 152 would further enhance the smooth and wrinkle-free molding of separation membrane 145 against the nozzle portion 141 during the fabrication of a funnel assembly of this construction.

Further to the above and with reference to FIGS. 22 and 23, frame 146 may comprise a band- or ring-like structure for application over nozzle portion 141 as shown, to retain separation membrane 145 securely in place. To enhance the wrinkle-free application and retention of separation membrane 145 against nozzle portion 141, nozzle portion 141 may define lateral bevels 153 along the leading edges distal to funnel holder 137. Bevels 153 serve to further reduce the angle of curvature and consequent shear and distention that may be imposed on separation membrane 145 in the fabrication of funnel assembly 135.

A further characteristic of this construction is illustrated in FIGS. 22 and 23, where it can be seen that the dimensions of separation membrane 145 are such as to achieve an overlap along the marginal edges of nozzle portion 141. Thus, the edges 154 of separation membrane 145 can be seen to extend around and up the sides of nozzle portion 141.

This further assists in achieving the wrinkle-free application and disposition of separation membrane 145 in the finally assembled funnel assembly 135 of this illustrated embodiment.

In accordance with an alternate embodiment of the invention illustrated in FIGS. 2-4, 9 and 10, funnel assembly comprises a funnel holder or a snap-in member 35 is adapted to be removably connected within the depressions 28 and 29 defined by the cover member 25. The snap-in member 35 has an elongated opening 36 which is of the same size and shape as the opening 29 of the cover member 25. An elongated funnel member 40 has a hollow nozzle portion 41 which fits through the opening 36. An externally projecting rim 42 of the funnel member 40 mates with the top face 37 of the snap-in member 35 and prevents the funnel member from passing through the opening 35. A separation membrane 45 is positioned at the bottom of funnel 40 and is held by the tapered shape of the funnel nozzle portion 41.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A medical diagnostic test kit for use with a body fluid of a patient comprising:
   (i) a bottom member forming a flat bottom wall and having joinder means to join said bottom member to a cover member defined below;
   (ii) an elongated dry chemistry test membrane having at least one reagent which reacts with said body fluid;
   (iii) a cover member having joinder means to join said cover member to said bottom member and having a receiving opening to receive said body fluid and a display window opening to display at least a part of said test membrane, wherein said test membrane is held between said bottom member and said cover member; and
   (iv) a removable funnel assembly comprising a funnel member that fits within the receiving opening of said cover member, having a hollow nozzle portion, a separation membrane in contact with said nozzle portion and extending arcuately about said nozzle portion and means to removably attach said funnel assembly to said cover member.

2. A kit as in claim 1 wherein said bottom member has a raised flange around said bottom wall.

3. A kit as in claim 1 and further including a flange integral with said bottom member and forming an elongated cavity.

4. A kit as in claim 3 wherein said membrane is positioned within said elongated cavity.

5. A kit as in claim 1 wherein said test membrane is positioned in contact with said receiving opening and said display window opening.

6. A kit as in claim 1 wherein said funnel assembly comprises a funnel holder having means to removably attach said funnel assembly to said cover member, a funnel member communicating with said funnel holder for receiving said patient's body fluid, said funnel member defining a nozzle portion, said nozzle portion defining at least one opening for egress of said body fluid toward said test membrane, and a separation membrane for filtration and delivery of said body fluid to said test membrane, said separation membrane being in substantially continuous contact with said nozzle portion and in substantially uniform fluid communication with said at least one opening defined therein.

7. A kit as in claim 6 wherein said separation membrane is non-adhesively held against said nozzle portion.

8. A kit as in claim 6 wherein said separation membrane, by means of enhanced surface juxtaposition achieved through compound curvature and projection thereof beyond said nozzle portion, makes capillary contact with said test membrane.

9. A kit as in claim 6 wherein said nozzle portion defines a plurality of openings.

10. A kit as in claim 9 wherein said nozzle portion defines a plurality of openings, and said frame member defines a plurality of openings for producing substantially uniform fluid communication with said openings in said nozzle portion.

11. A kit as in claim 6 wherein said funnel member further includes as a part thereof a frame member outwardly disposed with respect to said nozzle portion which engages and retains said nozzle portion, and cooperates with said nozzle portion to wrap and hold said separation membrane in sandwich-like relationship between said nozzle portion and said frame member, whereby said separation membrane is maintained in substantially continuous contact with said nozzle portion.

12. A kit as in claim 11 wherein said frame member defines a capturing rim for engagement of said funnel member and said separation membrane when said frame member is assembled therewith.

13. A kit as in claim 12 wherein said capturing rim defines means for the snap-fittable engagement of said funnel member.

14. A kit as in claim 12 wherein said capturing rim defines means for frictional engagement of said said separation membrane and said funnel member.

15. A kit as in claim 14 wherein said capturing rim defines a curved circumference along at least a part of a cross-section thereof for frictional engagement of said separation member and said funnel member.

16. A medical diagnostic test kit for use with a body fluid of a patient comprising:
   (i) a bottom member forming a rectangular flat bottom wall and having a raised flange around the bottom wall to join said bottom member to a cover member defined below, and an integral internal flange forming an elongated cavity;
   (ii) an elongated dry chemistry test membrane within said cavity and having at least one reagent which reacts with said patient's body fluid;
   (iii) an arcuate cover member having joinder means to join said cover member to said bottom member and having a receiving opening to receive said body fluid and a display window opening to display at least part of said membrane; where said membrane is held between said bottom member and said cover member and in contact with said receiving opening and said display window opening;
   (iv) a readily detachable funnel assembly comprising a funnel member having a hollow nozzle portion which fits within said receiving opening, means to removably attach said funnel assembly to said cover member, and a separation membrane means to separate red blood cells from serum and positioned in substantially uniform fluid communication with said nozzle portion.

17. A medical diagnostic test kit for use with a whole blood sample of a patient comprising:

(i) a bottom member forming a rectangular flat bottom wall and having a raised flange around the bottom wall to join said bottom member to a cover member defined below, and an integral internal flange forming an elongated cavity;

(ii) an elongated dry chemistry test membrane within said cavity and having at least one reagent which reacts with said patient's whole blood sample;

(iii) an arcuate cover member having joinder means to join said cover member to said bottom member and having a receiving opening to receive said body fluid and a display window opening to display at least part of said membrane; where said membrane is held between said bottom member and said cover member and in contact with said receiving opening and said display window opening;

(iv) a funnel assembly comprising a funnel member having a hollow nozzle portion which fits within said receiving opening, wherein said funnel assembly is permanently attached to said cover member.

* * * * *